(12) United States Patent
Fryburg et al.

(10) Patent No.: US 6,683,080 B2
(45) Date of Patent: Jan. 27, 2004

(54) TREATMENT OF DIABETES MELLITUS

(75) Inventors: David A. Fryburg, East Lyme, CT (US); Earl M. Gibbs, Oakdale, CT (US); Nandan P. Koppiker, Sandwich (GB)

(73) Assignee: Pfizer Inc., New York, NY (US)

( * ) Notice: Subject to any disclaimer, the term of this patent is extended or adjusted under 35 U.S.C. 154(b) by 24 days.

(21) Appl. No.: 10/060,788

(22) Filed: Jan. 30, 2002

(65) Prior Publication Data

US 2002/0143015 A1 Oct. 3, 2002

Related U.S. Application Data

(60) Provisional application No. 60/266,083, filed on Feb. 2, 2001.

(30) Foreign Application Priority Data

Mar. 15, 2001 (GB) ................................................ 0106468

(51) Int. Cl.[7] ................................................. A61K 31/53
(52) U.S. Cl. ....................... 514/242; 514/243; 514/246; 514/866
(58) Field of Search ................................ 514/242, 243, 514/246, 866

(56) References Cited

FOREIGN PATENT DOCUMENTS

| WO | WO9924433 | 5/1999 | ......... C07D/487/04 |
| WO | 1070705 | 1/2001 | ......... C07D/209/12 |
| WO | WO0119357 | 3/2001 | .......... A61K/31/00 |
| WO | 1088824 | 4/2001 | ......... C07D/495/04 |
| WO | WO0178781 | 10/2001 | .......... A61K/45/00 |

OTHER PUBLICATIONS

Goldstein et al., "Long–term efficacy and safety of vardenafil in diabetic men with erectile dysfunction", Diabetes, 2002, vol. 51, 2 (Jun.), PA98–A98.*

New Erectile Dysfunction Drug Useful In Diabetes Pharmaceutical Journal Nov. 10, 2001. p. 669.*

Vardenafil Improves Erectile Function In Men With Diabetes Pharmaceutical Journal Jul. 7, 2001. p. 9.*

* cited by examiner

*Primary Examiner*—Kevin E. Weddington
(74) *Attorney, Agent, or Firm*—Richard C. Richardson; Gregg C. Benson; A. Dean Olson

(57) ABSTRACT

Use of vardenafil or a pharmaceutical composition thereof in the preparation of a medicament for the curative, palliative or prophylactic treatment of type 2 diabetes mellitus.

4 Claims, No Drawings

TREATMENT OF DIABETES MELLITUS

This application claims priority from U.S. Provisional Application No. 60/266,083 filed Feb. 2, 2001, and U.K. Application 0106468.2 filed Mar. 15, 2001.

This invention relates to the use of particular potent and selective cGMP PDE5 inhibitor compounds and especially the compound vardenafil for the treatment of diabetes mellitus.

The revised classification of diabetes mellitus as detailed in Harrisons at Chapter 334: Diabetes Mellitus by J. Larry Jameson contains four major groups as listed below. In general, this classification is based upon the etiology of diabetes as it is currently understood. The term insulin dependant diabetes mellitus (IDDM) has been replaced by Type 1 diabetes. These patients have β-cell destruction, which is usually immune-mediated; most develop absolute insulin deficiency and are ketosis-prone. The term non-insulin dependant diabetes mellitus (NIDDM) has been replaced by Type 2 diabetes, which encompasses the most prevalent form of the disease. Most patients with Type 2 diabetes exhibit insulin resistance and ultimately develop a concomitant insulin secretory defect. The third class includes genetic defects in insulin secretion and action, diseases of the exocrine pancreas, endocrinopathies that induce hyperglycemia, drug-induced forms of diabetes, infectious causes of diabetes, and genetic syndromes that are associated with an increased incidence of diabetes. Gestational diabetes mellitus (GDM) remains a separate class.

Etiologic Classification of Diabetes Mellitus

I. Type 1 diabetes* β-cell destructions, usually leading to absolute insulin deficiency: A. Immune-mediated; B. Idiopathic II. Type 2 diabetes* (may range from predominantly insulin resistance with relative insulin deficiency to a predominantly secretory defect with insulin resistance)

III. Other specific types:
  A. Genetic defects of β-cell function such as: chromosome 12, HNF-1 α-(formerly MODY3); chromosome 7, glucokinase (formerly MODY2); chromosome 20, HNF-4 α-(formerly MODY1); mitochondrial DNA.
  B. Genetic defects in insulin action such as: Type A insulin resistance; leprechaunism; Rabson-Mendenhall syndrome; lipoatrophic diabetes.
  C. Diseases of the exocrine pancreas such as: pancreatitis; trauma/pancreatectomy; neoplasia; cystic fibrosis; hemochromatosis; fibrocalculous pancreatopathy.
  D. Endocrinopathies such as: acromegaly; Cushing's syndrome; glucagonoma; pheochromocytoma; hyperthyroidism; somatostatinoma; aldosteronoma.
  E. Drug- or chemical-induced such as: vacor; pentamdine; nicotinic acid; gluocorticoids; thyroid hormone; diazoxide; β-adrenergic agonists; thiazides; dilantin; α-interferon.
  F. Infections such as: congential rubella; cytomegalovirus.
  G. Uncommon forms of immune-mediated diabetes such as: "stiff-man" syndrome; anti-insulin receptor antibodies.
  H. Other genetic syndromes sometimes associated with diabetes such as: Down's syndrome; Klinefelter's syndrome; Turner's syndrome; Wolfram's syndrome; Friedrich's ataxia; Huntington's chorea; Lawrence Moon Beidel syndrome; myotonic dystrophy; porphyria; Prader Willi syndrome.

IV. Gestational diabetes mellitus (GDM)

* Patients with any form of diabetes may require insulin treatment at some stage of their disease. Such use of insulin does not, of itself, classify the patient.

Source: The expert Committee on the Diagnosis and Classification of Diabetes Mellitus, 1997.

It has been estimated that there will be 154,392,000 diabetics world-wide in the year 2000. Of these, 15,000,000 will be in the US and 934,000 in the UK. The burden of diabetes in both sexes in the WHO region estimated for 1998 was 11,668,000. Thus there exists a large medical need for an effective and safe oral therapy for the treatment of type 2 diabetes mellitus.

It is proposed herein that successful diagnosis and treatment of patients with type 2 diabetes mellitus may lead to a reduction in the risk of the development of cardiovascular disease in some of these patients. The primary pathology in diabetes mellitus is an inability to effectively control glucose. The underlying defect differs between the types of diabetes as outlined hereinbefore.

According to the present invention there is provided a method of treating type 2 diabetes mellitus in a mammal comprising administering to said mammal an effective amount of vardenafil or a pharmaceutically acceptable salt, solvate or composition thereof.

It is proposed herein that successful diagnosis and treatment of patients with type 2 diabetes mellitus may lead to a reduction in the risk of the development of cardiovascular disease in some of these patients.

The primary pathology in diabetes mellitus is an inability to effectively control glucose. The underlying defect differs between the types of diabetes as outlined hereinbefore.

In type 2 diabetes mellitus, resistances to the effects of insulin (insulin resistance) are manifest in the metabolic target organs such as the liver, adipose tissue and skeletal muscle. Metabolic pathways affected by insulin resistance include: glycogenesis, glycolysis, gluconeogenesis and the GLUT-4 transport mechanism as well as lipogenesis, lipolysis and protein synthesis within liver and muscle cells.

Resistance to the effects of insulin can also be observed in the diminished biological response of the endothelium to the vascular effects of insulin. That is, insulin promotes relaxation of blood vessel(s) at least in part through the action of nitric oxide. Nitric oxide generated in the endothelium then stimulates cGMP production in blood vessels and causes them to relax or dilate. This opening of the blood vessel allows more blood to flow, which is particularly important when more blood flow is needed to critical organs, like the heart. It has been demonstrated that there is a decreased release of nitric oxide (NO) from the endothelium of patients with insulin resistance. This decreased release of nitric oxide is not only from insulin, but also from other important vasodilators like acetylcholine. It is thought that the vascular effect of insulin contributes to the effect of insulin to regulate metabolism, particularly, but not necessarily limited to, glucose metabolism.

In addition to the vascular actions of nitric oxide, NO also has direct effects on glucose uptake by skeletal muscle. That is, treatment with a NO-donor substance (nitroprusside) or an analogue of cGMP treatment in vitro increases glucose uptake (transport by GLUT4 glucose transporters). This vasodilation-independent pathway is described in G. J. Etgen, D. A. Fryburg and E. M. Gibbs in *Diabetes*, 46, 1997 pp. 1915–1919 the contents of which are incorporated herein by reference. It is proposed herein that, taken together, nitric oxide and cGMP likely have direct tissue level and vascular actions that influence, mediate, or mimic insulin's actions.

In a "normal" physiology NO diffuses through the endothelial layer and produces vascular smooth muscle cell (VSMC) relaxation and through activation of guanylate cyclase and cyclic guanosine monophosphate production, brings about a vascular dilatation (vasodilation). It is believed that on a chronic basis impaired response to insulin and associated reduced NO release and related vasodilation can lead to migration and multiplication of VSMC cells under the endothelial layer which can cause atherosclerosis.

Individuals with type 2 diabetes mellitus have varying degrees of insulin sensitivity (insulin resistance), by virtue of their type 2 diabetes mellitus/glucose intolerance and hence have an inefficient insulin dependant pathway.

Whilst type 2 diabetes mellitus has many manifestations it is proposed herein that an important underlying mechanistic basis for the condition resides in a resistance to both the vascular and metabolic effects of insulin. It is also understood that the underlying pathology of vascular resistance in type 2 diabetes mellitus, is a diminished amount of NO produced by the endothelial cells in response to insulin. In the insulin pathway in insulin resistant individuals, there may be impaired signalling of insulin for glucose uptake (via the phosphatidylinositol 3-kinase, PI3-K, pathway) which may lead to an inefficient GLUT-4 transport mechanism. Whilst not wishing to be bound by any particular theory it is further proposed herein that the pathway for the GLUT-4 transport mechanism and cGMP-NO mechanistic pathway are somehow inter-linked.

For optimal functioning of the insulin signalling pathway for glucose uptake (via the GLUT-4 transport mechanism) it is preferable to have a normally functioning NO-cGMP pathway.

It is further proposed herein that amplification of the cGMP signal, using cGMP specific PDE5 inhibitors in patients with type 2 diabetes mellitus would help to optimise the insulin glucose uptake signal and improve insulin action at key tissues.

By making tissues more sensitive to insulin, it is thereby also proposed herein that improvements in the clinical parameters of type 2 diabetes mellitus would result, including, but not limited to improvements in:

1. Blood glucose control: In patients with diabetes mellitus or impaired glucose tolerance (IGT), it is postulated herein that an improvement in insulin resistance should result in a decrease in plasma glucose concentrations (either fasting or after an oral glucose tolerance test or a meal). In a related manner, as regulated by the patient's pathophysiology, there will likely be an improvement in serum insulin concentrations in either the fasting state or after a glucose load or meal. These improvements in blood glucose control, should the subjects have type 2 diabetes mellitus, would manifest as improvements in measures of long-term blood glucose control, such as, but not limited to, haemoglobin A1c (glycosylated haemoglobin) or fructosamine; and/or
2. Blood pressure: It is postulated herein that an improvement in insulin resistance may also yield improvements in both systolic and diastolic blood pressure; and/or
3. Lipids: It is postulated herein that an improvement in insulin resistance may also yield improvements in serum lipids, including, but not limited to, serum cholesterol and triglycerides; and/or
4. Uric Acid: It is postulated herein that an improvement in insulin resistance may also yield improvements in serum uric acid; and/or
5. Coagulation Factors: It is postulated herein that an improvement in insulin resistance would also restore, towards normal, factors that worsen the procoagulant state.

These improvements in insulin resistance (improved sensitivity) may or may not be accompanied by improvement in compensatory hyperinsulinaemia.

cGMP PDE 5 inhibitors prevent the effect of the phosphodiesterase 5 enzyme that converts cGMP to inactive GMP thus increasing the amount of accumulated cGMP. This accumulation would amplify the vasodilatory and anti-atherogenic effects of the available nitric oxide and insulin. It is postulated herein that this amplification action (of cGMP) will reduce the compensatory hyperinsulinaemia seen in individuals with type 2 diabetes mellitus and hence decrease the atherogenic consequence of excessive signalling through the intact MAP kinase pathway (as detailed hereinbefore).

cGMP PDE 5 inhibitors prevent the effect of the phosphodiesterase 5 enzyme that converts cGMP to inactive GMP thus increasing the amount of accumulated cGMP. This accumulation would amplify the vasodilatory and anti-atherogenic effects of the available nitric oxide and insulin. It is postulated herein that this will amplification action (of plasma cGMP) will reduce the compensatory hyperinsulinaemia seen in individuals with type 2 diabetes mellitus and hence decrease the atherogenic consequence of excessive signalling through the intact MAP kinase pathway (as detailed hereinbefore).

cGMP PDE 5 inhibitors prevent the effect of the phosphodiesterase 5 enzyme that converts cGMP to inactive GMP thus increasing the amount of accumulated cGMP and amplifying the vasodilatory and anti-atherogenic effects of the available nitric oxide and insulin. It is postulated herein that this will amplification action will reduce the compensatory hyperinsulinaemia seen in individuals with type 2 diabetes mellitus and hence decrease the atherogenic consequence of excessive signalling through the intact MAP kinase pathway (as detailed hereinbefore).

Vardenafil is an imidazotriazinone compound which is a potent and selective inhibitor of cyclic guanosine monophosphate (cGMP) specific phosphodiesterase type 5 (PDE5) which is the predominant PDE5 isoenzyme in human corpora cavernosa. It is proposed herein that by inhibiting the cGMP to GMP conversion pathway, selective cGMP PDE5 inhibitors and in particular vardenafil increase the intracellular concentrations of nitric oxide (NO) derived cGMP, thereby enhancing the effect of NO, and thus can amplify the vasodilatory and anti-atherogenic effects of the available NO and insulin in subjects with type 2 diabetes mellitus.

Thus according to a first aspect of the present invention we provide a method of treating a patient with type 2 diabetes mellitus which comprises treating the patient with an effective amount of vardenafil or a pharmaceutical composition thereof or a pharmaceutically or veterinarily acceptable salt thereof, or a pharmaceutically or veterinarily acceptable solvate of either entity.

For the avoidance of doubt vardenafil as defined herein is 2-[2-Ethoxy-5-(4-ethyl-piperazin-1-yl-1-sulphonyl)-phenyl]-5-methyl-7-propyl-3H-imidazo[5,1-f][1,2,4]triazin-4-one which is also known as 1-[[3-(3,4-dihydro-5-methyl-4-oxo-7-propylimidazo[5,1-f]]-as-triazin-2-yl)-4-ethoxyphenyl]sulphonyl]-4-ethylpiperazine. Methods for the preparation of vardenafil are published in PCT application WO99/24433, see the compound of examples 20, 19, 337 and 336.

According to a further aspect of the present invention there is provided the use of IC-351 or a pharmaceutical composition or a pharmaceutically or veterinarily acceptable salt thereof, or a pharmaceutically or veterinarily acceptable solvate in the preparation of a medicament for the curative, palliative or prophylactic treatment of type 2 diabetes mellitus. For the avoidance of doubt IC-351 as defined herein is (6R, 12aR)-2,3,6,7,12,12a-hexahydro-2-methyl-6-(3,4-methylenedioxyphenyl)-pyrazino[2',1':6,1]pyrido[3,4-b]indole-1,4-dione (IC-351), the compound of examples 78 and 95 of published international application WO95/19978.

According to a yet further aspect of the present invention the following compounds are also useful for the treatment of diabetes mellitus: the compounds of examples 1, 3, 7 and 8; and the compound of example 11 of published international application WO93/07124 (EISAI); the quinazolin-4-ones disclosed in published international patent application WO93/12095; the pyrido [3,2-d]pyrimidin-4-ones disclosed in published international patent application WO 94/05661; the purin-6-ones disclosed in published international patent application WO 94/00453; the purinone compounds disclosed in pending British patent application GB-A-9924020.2; of particular interest according to this further aspect are the compounds disclosed in published international application WO95/19978; the compounds disclosed in published international application WO 99/24433 and the compounds disclosed in published international application WO 93/07124.

Still other type 5 phosphodiesterase inhibitors useful for the treatment of type 2 diabetes mellitus in conjunction with the present invention include: 4-bromo-5-(pyridylmethylamino)-6-[3-(4-chlorophenyl)-propoxy]-3 (2H)pyridazinone; 1-[4-[(1,3-benzodioxol-5-ylmethyl) amiono]-6-chloro-2-quinozolinyl]-4-piperidine-carboxylic acid monosodium salt; (+)-cis-5,6a,7,9,9,9a-hexahydro-2-[4-(trifluoromethyl)-phenylmethyl-5-methyl-cyclopent-4,5] imidazo[2,1-b]purin-4(3H)one; furazlocillin; cis-2-hexyl-5-methyl-3,4,5,6a,7,8,9,9a-octahydrocyclopent[4,5]-imidazo [2,1-b]purin-4-one; 3-acetyl-1-(2-chlorobenzyl)-2-propylindole-6-carboxylate; 3-acetyl-1-(2-chlorobenzyl)-2-propylindole-6-carboxylate; 4-bromo-5-(3-pyridylmethylamino)-6-(3-(4-chlorophenyl) propoxy)-3-(2H)pyridazinone; 1-methyl-5(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl) amino]-6-chloro-2-quinazolinyl]-4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough); GF-196960 (Glaxo Wellcome); E-8010(E-4010 (Eisai); Bay-38-3045 & 38-9456 (Bayer) and Sch-51866.

The suitability of any particular cGMP PDE5 inhibitor for use in the treatment of type 2 diabetes mellitus according to the present invention can be readily determined by evaluation of its potency and selectivity using literature methods followed by evaluation of its toxicity, absorption, metabolism, pharmacokinetics, etc in accordance with standard pharmaceutical practice as well as by the test methods detailed herein.

More particularly, the present invention provides a method of treating a patient with type 2 diabetes mellitus which comprises treating the patient with an effective amount of vardenafil or pharmaceutically acceptable salts, solvates, pro-drugs, polymorphs or pharmaceutical compositions thereof.

The invention also provides for the use of a vardenafil for the manufacture of a composition for the treatment or prophylaxis of type 2 diabetes mellitus.

The pharmaceutically acceptable salts of vardenafil for use in the present invention which contain a basic centre are, for example, non-toxic acid addition salts formed with inorganic acids such as hydrochloric, hydrobromic, hydroiodic, sulphuric and phosphoric acid, with carboxylic acids or with organo-sulphonic acids. Examples include the HCl, HBr, HI, sulphate or bisulphate, nitrate, phosphate, or hydrogen, phosphate, acetate, benzoate, succinate, saccarate, fumarate, maleate, lactate, citrate, tartrate, gluconate, camsylate, methanesulphonate, ethanesulphonate, benzene-sulphonate, p-toluene-sulphonate, phenylsulphonate, napthalenesulphonate and pamoate salts. Ammonium salts or salts derived from organic amines of vardenafil for example, ethylamine, di- or triethylamine, di- or triethanolamine, dicyclohexylamine, dimethylaminoethanol, arginine, lysine, ethylenediamine or 2-phenylethylamine are also pharmaceutically acceptable for use herein. Vardenafil can also provide pharmaceutically acceptable metal salts, in particular non-toxic alkali and alkaline earth metal salts, with bases. Examples include the sodium, potassium, aluminium, calcium, magnesium, zinc and diethanolamine salts. For a review on suitable pharmaceutical salts see Berge et al, J. Pharm, Sci., 66, 1–19, 1977.

Vardenafil useful for the treatment of type 2 diabetes mellitus according to the present invention, its pharmaceutically acceptable salts, and pharmaceutically acceptable solvates can be administered alone but, in human therapy will generally be administered in admixture with a suitable pharmaceutical excipient diluent or carrier selected with regard to the intended route of administration and standard pharmaceutical practice.

For example, vardenafil or salts or solvates thereof can be administered orally, buccally or sublingually in the form of tablets, capsules (including soft gel capsules), ovules, elixirs, solutions or suspensions, which may contain flavouring or colouring agents, for immediate-, delayed-, modified-, or controlled-release such as sustained-, dual-, or, pulsatile delivery applications. Vardenafil may also be administered via fast dispersing or fast dissolving dosages forms or in the form of a high energy dispersion or as coated particles.

Vardenafil can also be administered parenterally, for example, intracavernosally, intravenously, intra-arterially, intraperitoneally, intrathecally, intraventricularly, intraurethrally intrasternally, intracranially, intramuscularly or subcutaneously, or may be administered by infusion or needleless injection techniques.

For oral and parenteral administration to human patients, the daily dosage level of vardenafil or salts or solvates thereof will usually be from 10 to 500 mg (in single or divided doses). For the treatment of type 2 diabetes mellitus the dosage may by via single dose, divided daily dose, multiple daily dose, continuous (chronic) daily dosing for a specified period which may be from one to five or 5 or more, such as up to 10 or more days. Alternatively the treatment of type 2 diabetes mellitus may be affected by continuous dosing, such as for example, via a controlled release dosage form wherein such continuous dosage form can be administered on a daily basis for a number of days or wherein such continuous dosing can be affected via a slow-release formulation which doses for more than one day at a time.

For human use, in the case of oral administration, it is good practice to administer doses of vardenafil from 0.001 to 50 mg/kg, preferably of 0.01 mg/kg–20 mg/kg. In the case of parenteral administration, such as, for example, via mucous membranes nasally, buccally or inhalatively, it is good practice to use doses of 0.001 mg/kg–0.5 mg/kg.

Thus, for example, tablets or capsules of vardenafil or salts or solvates thereof may contain from 5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

Vardendafil can also be administered intranasally or by inhalation. Vardenafil may also be formulated for delivery via an atomiser or in the form of a suppository or pessary, or may be applied topically in the form of a gel, hydrogel, lotion, solution, cream, ointment or dusting powder. Vardenafil or salts or solvates thereof may also be dermally administered, or transdermally administered, for example, by the use of a skin patch and may also be administered by the ocular, pulmonary or rectal routes.

Generally, in humans, oral administration of vardenafil is the preferred route, being the most convenient. In circumstances where the recipient suffers from a swallowing disorder or from impairment of drug absorption after oral administration, the drug may be administered parenterally, sublingually or buccally.

For veterinary use, vardenafil, or a veterinarily acceptable salt thereof, or a veterinarily acceptable solvate or pro-drug thereof, is administered as a suitably acceptable formulation in accordance with normal veterinary practice and the veterinary surgeon will determine the dosing regimen and route of administration which will be most appropriate for a particular animal.

The aforementioned routes of administration and formulations are also applicable to the use of IC-351 for the treatment of IC-351 for the treatment of type 2 diabetes mellitus as defined hereinbefore.

The present invention additionally comprises treatment of types 2 diabetes mellitus with a combination of vardenafil as defined herein with:

1) one or more naturally occurring or synthetic prostaglandins or esters thereof. Suitable prostaglandins for use herein include compounds such as alprostadil, prostaglandin $E_1$, prostaglandin $E_0$, 13, 14-dihydroprosta glandin $E_1$, prostaglandin $E_2$, eprostinol, natural synthetic and semi-synthetic prostaglandins and derivatives thereof including those described in WO-00033825 and/or U.S. Pat. No. 6,037,346 issued on Mar. 14, 2000 all incorporated herein by reference, $PGE_0$, $PGE_1$, $PGA_1$, $PGB_1$, $PGF_1$ α, 19-hydroxy $PGA_1$, 19-hydroxy-$PGB_1$, $PGE_2$, $PGB_2$, 19-hydroxy-$PGA_2$, 19-hydroxy-$PGB_2$, $PGE_3$α, carboprost tromethamine dinoprost, tromethamine, dinoprostone, lipo prost, gemeprost, metenoprost, sulprostune, tiaprost and moxisylate; and/or 2) one or more α—adrenergic receptor antagonist compounds, α-blockers. Suitable compounds for use herein include: the α-adrenergic receptor blockers as described in PCT application WO99/30697 published on Jun. 14, 1998, the disclosures of which relating to α-adrenergic receptors are incorporated herein by reference and include, selective $α_1$-adrenoceptor or $α_2$-adrenoceptor blockers and non-selective adrenoceptor blockers, suitable $α_1$-adrenoceptor blockers include: phentolamine, phentolamine mesylate, trazodone, alfuzosin, indoramin, naftopidil, tamsulosin, dapiprazole, phenoxybenzamine, idazoxan, efaraxan, yohimbine ($α_2$-blocker), rauwolfa alkaloids, Recordati 15/2739, SNAP 1069, SNAP 5089, RS17053, SL 89.0591, doxazosin, terazosin, abanoquil and prazosin;

$α_2$-blocker blockers from U.S. Pat. No. 6,037,346 [Mar. 14, 2000] dibenarnine, tolazoline, trimazosin and dibenarnine; α-adrenergic receptors as described in U.S. Pat. Nos. 4,188,390; 4,026,894; 3,511,836; 4,315,007; 3,527,761; 3,997,666; 2,503,059; 4,703,063; 3,381,009; 4,252,721 and 2,599,000 each of which is incorporated herein by reference; $α_2$-Adrenoceptor blockers include: clonidine, papaverine, papaverine hydrochloride, optionally in the presence of a cardiotonic agent such as pirxamine; and/or 3) one or more NO-donor (NO-agonist) compounds. Suitable NO-donor compounds for use herein include organic nitrates, such as mono- di or tri-nitrates or organic nitrate esters including glyceryl trinitrate (also known as nitroglycerin), isosorbide 5-mononitrate, isosorbide dinitrate, pentaerythritol tetranitrate, erythrityl tetranitrate, sodium nitroprusside (SNP), 3-morpholinosydnonimine molsidomine, S-nitroso-N-acetyl penicilliamine (SNAP) S-nitroso-N-glutathione (SNO—GLU), N-hydroxy-L-arginine, amylnitrate, linsidomine, linsidomine chlorohydrate, (SIN-1) S-nitroso-N-cysteine, diazenium diolates,(NONOates), 1,5-pentanedinitrate, L-arginine, ginseng, zizphi fructus, molsidomine, Re-2047, nitrosylated maxisylyte derivatives such as NMI-678-11 and NMI-937 as described in published PCT application WO 0012075; and/or 4) one or more potassium channel openers or modulators. Suitable potassium channel openers/modulators for use herein include nicorandil, cromokalim, levcromakalim, lemakalim, pinacidil, cliazoxide, minoxidil, charybdotoxin, glyburide, 4-amini pyridine, $BaCl_2$; and/or 5) one or more dopaminergic agents, preferably apomorphine or a selective D2, D3 or D2/$D_3$ agonist such as, pramipexole and ropirinol (as claimed in WO-0023056), L-Dopa or carbidopa, PNU95666 (as claimed in WO-0040226); and/or 6) one or more vasodilator agents. Suitable vasodilator agents for use herein include nimodepine, pinacidil, cyclandelate, isoxsuprine, chloroprumazine, halo peridol, Rec 15/2739, trazodone, and/or 7) one or more thromboxane A2 agonists; and/or 8) one or more ergot alkaloids; Suitable ergot alkaloids are described in U.S. Pat. No. 6,037,346 issued on Mar. 14, 2000 and include acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, terguride; and/or 9) one or more compounds which modulate the action of natruretic factors in particular atrial naturetic factor (also known as atrial naturetic peptide), B type and C type naturetic factors such as inhibitors of neutral endopeptidase; and/or 10) one or more angiotensin receptor antagonists such as losartan; and/or 11) one or more substrates for NO-synthase, such as L-arginine; and/or 12) one or more calcium channel blockers such as amlodipine; and/or 13) one or more antagonists of endothelin receptors and inhibitors or endothelin-converting enzyme; and/or 14) one or more cholesterol lowering agents such as statins (e.g. atorvastatin/Lipitor-trademark) and fibrates; and/or 15) one or more antiplatelet and antithrombotic agents, e.g. tPA, uPA, warfarin, hirudin and other thrombin inhibitors, heparin, thromboplastin activating factor inhibitors; and/or 16) one or more insulin sensitising agents such as Avandia or Actos and hypoglycaemic agents such as, but not limited to, glipizide (sulfonylureas), metformin, or acarbose; and/or 17) one or more acetylcholinesterase inhibitors such as donezipil; and/or 18) one or more estrogen receptor modulators and/or estrogen agonists and/or estrogen antagonists, preferably raloxifene or lasofoxifene, (−)-cis-6-phenyl-5-[4-(2-pyrrolidin-1-yl-ethoxy)-phenyl]-5,6,7,8-tetrahydronaphthalene-2-ol and pharmaceutically acceptable salts thereof (compound A below) the preparation of which is detailed in WO 96/21656.

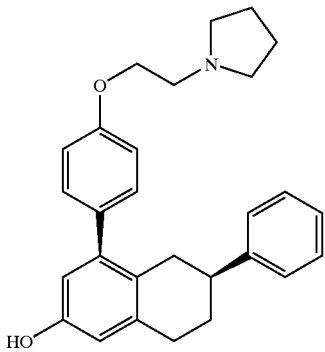

Compound A 19) one or more of a further PDE inhibitor, more particularly a PDE 2, 4, 7 or 8 inhibitor, preferably a PDE2 inhibitor said inhibitors preferably having an IC50 against the respective enzyme of less than 100 nM: and/or 20) one or more of an NPY (neuropeptide Y) inhibitor, more particularly NPY1 or NPY5 inhibitor, preferably NPY1 inhibitor, preferably said NPY inhibitors (including NPY Y1 and NPY Y5) having an IC50 of less than 100 nM, more preferably less than 50 nM, suitable NPY and in particular NPY1 inhibitor compounds are described in EP-A-1097718; and/or 21) one or more of vasoactive intestinal peptide (VIP), VIP mimetic, more particularly mediated by one or more of the VIP receptor subtypes VPAC1, VPAC or PACAP (pituitary adenylate cyclase activating peptide), one or more of a VIP receptor agonist or a VIP analogue (eg Ro-125-1553) or a VIP fragment, one or more of a α-adrenoceptor antagonist with VIP combination (eg Invicorp, Aviptadil); and/or 22) one or more of a melanocortin receptor agonist or modulator or melanocortin enhancer, such as melanotan II, PT-14, PT-141 or compounds claimed in WO-09964002, WO-00074679, WO-09955679, WO-00105401, WO-00058361, WO-00114879, WO-00113112, WO-09954358; and/or 23) one or more of a serotonin receptor agonist, antagonist or modulator, more particularly agonists, antagonists or modulators for 5HT1A (including VML 670), 5HT2A, 5HT2C, 5HT3 and/or 5HT6 receptors, including those described in WO-09902159, WO-00002550 and/or WO-00028993; and/or 24) one or more of a testosterone replacement agent (inc dehydroandrostendione), testosternone (Tostrelle), dihydrotestosterone or a testosterone implant; and/or 25) one or more of estrogen, estrogen and medroxyprogesterone or medroxyprogesterone acetate (MPA) (i.e. as a combination), or estrogen and methyl testosterone hormone replacement therapy agent (e.g. HRT especially Premarin, Cenestin, Oestrofeminal, Equin, Estrace, Estrofem, Elleste Solo, Estring, Eastraderm TTS, Eastraderm Matrix, Dermestril, Premphase, Preempro, Prempak, Premique, Estratest, Estratest HS, Tibolone); and/or 26) one or more of a modulator of transporters for noradrenaline, dopamine and/or serotonin, such as bupropion, GW-320659; and/or 27) one or more of a purinergic receptor agonist and/or modulator; and/or 28) one or more of a neurokinin (NK) receptor antagonist, including those described in WO-09964008; and/or 29) one or more of an opioid receptor agonist, antagonist or modulator, preferably agonists for the ORL-1 receptor; and/or 30) one or more of an agonist or modulator for oxytocin/vasopressin receptors, preferably a selective oxytocin agonist or modulator; and/or 31) one or more modulators of cannabinoid receptors; and/or 32) one or more CNS active agents; and/or 33) one or more compounds which inhibit angiotensin-converting enzyme such as enapril, and one or more combined inhibitors of angiotensin-converting enzyme and neutral endopeptidase such as omapatrilat; and/or 34) L-DOPA or carbidopa; and/or 35) one or more steroidal or non-steroidal anti-inflammatory agents; and/or 36) one or more protein kinase C-β inhibitors such as LY333531; and/or 37) one or more activators of AMP-activated protein kinase such as 5-amino-4-imidazolecarboxamide ribonucleoside; and/or 38) insulin; and/or 39) weight loss agents such as sibutramine or orlistat; and/or 40) one or more dipeptidyl peptidase IV inhibitors such as NVP DPP728 or P32/98; and/or 41) one or more glucagon antagonists such as NNC25-2504; and/or 42) one or more agents that inhibit PTP1B such as PTP112; and/or 43) one or more agents that reduce PTP1B levels using antisense technology; and/or 44) one or more glycogen synthase kinase-3 inhibitors such as Chir98014; and/or 45) one or more GLP-1 agonists such as GLP1, NN-2211 or exendin 4; and/or 46) one or more PPAR-gamma agonists such as Avandia, Actos or CS011; and/or 47) one or more PPAR-alpha agonists such as fenofibrate; and/or 48) one or more dual PPAR-alpha/PPAR-gamma agonists such as farglitazar, rosiglitasone, pioglitazone, GW1929, DRF2725, AZ242 or KRP 297; and/or 49) one or more sorbitol dehydrogenase inhibitors such as CP-470711; and/or 50) one or more aldose reductase inhibitors such as zopolrestat, zenarestat, or fidarestat; and/or 51) one or more preparations of growth hormone or growth hormone secretagogues; and/or 52) one or more of an NEP inhibitor, preferably wherein said NEP is EC 3.4.24.11 and more preferably wherein said NEP inhibitor is a selective inhibitor for EC 3.4.24.11, more preferably a selective NEP inhibitor is a selective inhibitor for EC 3.4.24.11, which has an $IC_{50}$ of less than 100 nM (e.g. ompatrilat, sampatrilat) suitable NEP inhibitor compounds are described in EP-A-1097719.

Preferred combinations for use according to the present invention include the combination vardenafil with (36), (37), (38) or (39) as detailed hereinbefore.

The aforementioned combinations, including the preferred combinations are also applicable to the use of IC-351 for the treatment of IC-351 for the treatment of type 2 diabetes mellitus as defined hereinbefore.

It is to be appreciated that all references herein to treatment include curative, palliative and prophylactic treatment.

The effect of vardenafil against key parameters associated with type 2 diabetes mellitus can be determined by testing an effective amount of vardenafil in the following experimental protocols.

Protocols to Measure the Effect on Insulin Resistance Syndrome in Animals—Effects on Plasma Glucose and Serum Triglyceride Levels in ob/ob Mice

EXPERIMENTAL PROTOCOL

Effective Amount of Test Compound

An effective amount of vardenafil for use in the experimental protocols hereinafter can be determined by measurement of the pharmacokinetic/pharmacodynamic profile of vardenafil in diabetic mice. Such pharmacokinetic/pharmacodynamic profile can be determined by standard procedures as are known to the skilled pharmacologist as described hereinafter.

Test Compound

The compound to be tested is solubilized in 10% DMSO/0.1% pluronics and dosed via oral gavage using mouse oral feeding needles (20 gauge, Popper & Sons, Inc., New Hyde Park, N.Y.). An effective amount (ml/kg weight) is administered for each dose. Compounds can be tested at doses ranging from 1–50 mg/kg. Alternatively, the test compound can be administered in the drinking water.

Experimental Animals:

Male ob/ob mice such as those obtained from Jackson Laboratories (Bar Harbor, Me.) can be used in the studies at 6 to 10 weeks of age. Mice are to be housed five per cage and allowed free access to D11 mouse chow (Purina, Brentwood, Mo.) and water.

Pharmacokinetic/Pharmacodynamic Protocol:

Mice are allowed to acclimate to the Pfizer animal facilities for 1 week prior to the start of the study. Mice are sorted into groups of three and dosed with test compound. At time zero and various time points thereafter mice are killed by decapitation and blood collected for plasma preparation as described hereinafter. Plasma is then analyzed for test compound and cGMP levels as described hereinafter. Plasma drug levels are used to calculate phamacokinetic parameters of the test compound using Winnonlin analysis. Plasma cGMP levels over the time course of the study define the pharmacodynamic profile, which is compared to the pharmacokinetic profile to determine appropriate dosing paradgims for subsequent multiple dose studies.

Multiple Dose Protocol:

Experimental Protocol:

Mice are allowed to acclimate to the Pfizer animal facilities for 1 week prior to the start of the study. On day one, retro-orbital blood samples are to be obtained and plasma glucose to be determined as described hereinafter. Mice are then sorted into groups of five such that mean plasma glucose concentrations for each group does not differ. On day one mice are dosed with vehicle or an effective amount of test compound only in the afternoon. Subsequently, mice are to be dosed twice a day on day 2–4 in the morning and in the afternoon. On day 5, the mice receive an a.m. dose and are to be bled 3 hours later for plasma preparation for glucose and triglyceride analysis as described below. Alternatively, test compound can be administered in the drinking water commencing on the afternoon of day 1 and continuing through day 5, when mice are then bled for plasma preparation for glucose and triglyceride analysis as described below. Terminal plasma samples are collected on day 5 following the retro-orbital sinus bleed as described below. Body weight is measured on days 1 and 5 of the study, and food consumption is assessed over the 5 day period.

Terminal Bleed and Tissue Collection:

On the morning of the last day of the study mice are dosed with test compound or vehicle at approximately 8:00 am. Three hours after dosing, 25 $\mu$L of blood is obtained via the retro-orbital sinus and added to 100 $\mu$L of 0.025% heparinized-saline in Denville Scientific microtubes. The tubes are spun at the highest setting in a Beckman Microfuge 12 for 2 minutes. Plasma is collected for plasma glucose and triglyceride determination. The mice are then sacrificed by decapitation and ~1 ml of blood is collected in Becton-Dickinson Microtainer brand plasma separator tubes with lithium heparin. The tubes are spun in a Beckman Microfuge 12 at the maximum setting for five minutes. Plasma is collected in 1.5 ml Eppendorf tubes and snap frozen in liquid nitrogen. Plasma samples are stored at −80° C. until analyzed.

Metabolite and Hormone Analysis:

Plasma glucose and triglycerides can be measured using the Alcyon Clinical Chemistry Analyzer (Abbott Laboratories, Abbott Park, Ill.) using kits supplied by Abbott. Plasma cGMP can be measured using the Biotrak enzyme-immunoassay system by Amersham (Piscataway, N.J.). Via a similar technique the plasma insulin can be assessed by the Mercodia ELISA Insulin kit by ALPCO (Uppsala, Sweden). All assays are conducted according to instructions provided by the manufacturers.

Plasma Analysis of Test Compound Levels:

Quantitation of the compound to be tested is accomplished using an LC/MS/MS assay with a dynamic range of 0.01 to 10 $\mu$g/ml. Plasma standards of the compound to be tested are prepared by serial dilution of control ob/ob mouse plasma. A 20 $\mu$l aliquot of plasma is added to a 0.7 ml Qglass vial with 200 $\mu$l of a 0.1 $\mu$M solution of internal standard in 50% methanol/acetonitrile. The samples are then vortexed and spun at 3500 rpm for 3 minutes in an IEC Centra GP8% centrifuge (International Equipment Company, Needham Hieghts, Mass.). Following centrifugation, the samples are injected (3 $\mu$l) onto a Phenomenex Primesphere 2.0×30 mm 5 $\mu$m $C_{18}$ column at 25° C. with a run time of 3 minutes. Analytes are eluted with a gradient program consisting of 5% methanol ("A") and 95% 10 mM ammonium ("B") acetate at a flow rate of 0.5 ml/min for the first 30 seconds. Over the next 1.5 minutes, the flow rate is ramped to 0.75 mL/min at the same time that the A solvent is ramped to 95%. At two minutes, the concentrations of the A and B solvents (95 and 5%, respectively) are held constant for an additional thirty seconds, after which the concentrations are returned to the starting condition in a one-second step. The column is allowed to re-equilibrate for 30 seconds prior to the next injection. The column effluent entered the Turbo Ionspray source (500° C., 7 L/min of nitrogen) of a PE-Sciex API-3000 triple quadrupole mass spectrometer (Perkin Elmer-Sciex, Foster City, Calif.). Drug and internal standard are measured using multiple reaction monitoring (m/z= parent ion→fragmentation for drug and internal standard, respectively) at a retention time of 2.4 and 2.7 minutes, respectively. Peak area ratios of drug over internal standard are fit using linear least squares regression analysis with $1/x^2$ weighting.

Statistical Analysis:

Comparisons between drug treatments and appropriate vehicles can be done by Student's t-test.

Accordingly the present invention provides a method of treatment for type 2 diabetes mellitus with an effective amount of vardenafil as can be demonstrated by the experimental procedures and protocols described hereinbefore.

Results (Summary):

Sildenafil citrate (Viagra™), a potent and selective PDE5 inhibitor has been demonstrated to reduce the plasma glucose and serum triglyceride levels produced by ob/ob mice in accordance with the biological test methods detailed hereinbefore.

What is claimed is:

1. A method of treating type 2 diabetes mellitus in a mammal comprising administering to said mammal an effective amount of vardenafil or a pharmaceutically acceptable salt, solvate or composition thereof.

2. A method of treating type 2 diabetes mellitus in a mammal comprising administering to said mammal an effective amount of vardenafil or a pharmaceutically acceptable salt, solvate or composition thereof wherein said administration comprises daily dosing and wherein said dosing can be in the form of single, multiple or divided doses.

3. A method of treating type 2 diabetes mellitus in a mammal comprising administering to said mammal an effective amount of vardenafil or a pharmaceutically acceptable salt, solvate or composition thereof wherein said administration comprises daily dosing for 5 or more days wherein said daily dosing can be in the form of single, multiple or divided doses.

4. A method of treating type 2 diabetes mellitus in a mammal comprising administering to said mammal an effective amount of a vardenafil or a pharmaceutically acceptable salt, solvate or composition thereof wherein said administration comprises continuous dosing for 5 or more days wherein said continuous dosing can be in the form of single or multiple continuous release doses.

* * * * *